United States Patent [19]

Erpenbach et al.

[11] 4,260,520

[45] Apr. 7, 1981

[54] CARRIER-SUPPORTED CATALYST AND PROCESS FOR MAKING IT

[75] Inventors: Heinz Erpenbach, Cologne; Klaus Gehrmann; Herbert Joest, both of Erfstadt, all of Fed. Rep. of Germany

[73] Assignee: Hoechst Aktiengesellschaft, Frankfurt am Main, Fed. Rep. of Germany

[21] Appl. No.: 93,868

[22] Filed: Nov. 13, 1979

[30] Foreign Application Priority Data

Nov. 16, 1978 [DE] Fed. Rep. of Germany ....... 2849715

[51] Int. Cl.$^3$ .............................................. B01J 27/14
[52] U.S. Cl. .................................... 252/437; 252/435
[58] Field of Search ................................ 252/435, 437

[56] References Cited

U.S. PATENT DOCUMENTS

| 3,755,196 | 8/1973 | Mickelson | 252/437 X |
| 4,039,476 | 8/1977 | Bertus et al. | 252/435 X |
| 4,122,039 | 10/1978 | Kobylinski et al. | 252/437 X |

FOREIGN PATENT DOCUMENTS

1148108 4/1969 United Kingdom .

*Primary Examiner*—Delbert E. Gantz
*Assistant Examiner*—William G. Wright
*Attorney, Agent, or Firm*—Connolly and Hutz

[57] ABSTRACT

The invention relates to a carrier-supported catalyst comprising oxides of cobalt and phosphorus and at least one of the oxides of molybdenum and potassium in the atomic ratio of $Co_1P_{1-2}Mo_{0-0.05}K_{0-0.5}$ on a porous carrier material, and to a process for making it. To this end, the process provides (a) for a dry porous carrier material to be saturated with water up to 40 to 80% of its predetermined saturation value;

(b) for the carrier material treated as under (a) to be impregnated either at least once with an aqueous solution of water-soluble compounds of cobalt and phosphorus, molybdenum and/or potassium, or repeatedly and successively, each impregnation being interrupted by an intermediary drying period as specified under (c), with an aqueous solution of a water-soluble compound of merely one of the elements aforesaid, the aqueous solution being used in either case in a quantity which is at most necessary for complete saturation;

(c) for the carrier material to be dried after each impregnation over a period of 2 to 20 hours at 350 to 500 K; and (d) for the carrier material treated as described under (a) through (c) to be sintered over a period of 0.5 to 4 hours at 550 to 1000 K, in a stream of air.

The carrier-supported catalyst finds use in the production of styrene by subjecting ethylbenzene to oxidative dehydrogenation with molecular oxygen in gas phase.

9 Claims, 1 Drawing Figure

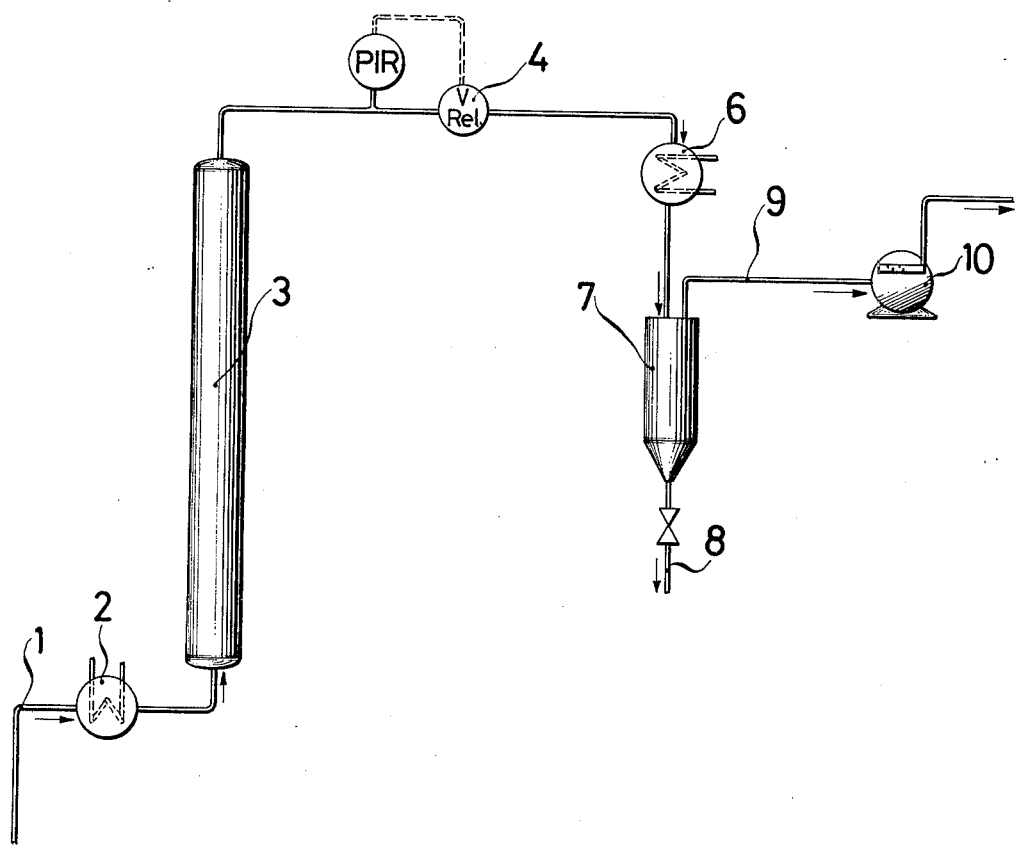

CARRIER-SUPPORTED CATALYST AND PROCESS FOR MAKING IT

The present invention relates to a carrier-supported catalyst, to a process for making it, and to its use in the production of styrene by subjecting ethylbenzene to an oxidative dehydrogenation reaction with molecular oxygen in gas phase.

Carrier-supported catalysts for use in the above reaction have already been described, e.g. in British Patent Specification No. 1,148,108, wherein ethylbenzene is subjected to oxidative dehydrogenation with air, in the presence of steam, at 350° to 600° C. and with the use of a flow bed catalyst consisting of chromium oxide and an alkali metal oxide which are deposited on a carrier. U.S. Pat. No. 3,917,732 describes a process, wherein the oxidative dehydrogenation is effected in the presence of a magnesium/nickel/pyrophosphate-catalyst and in the presence of helium, nitrogen or steam as an inert diluent. U.S. Pat. No. 3,923,916 discloses a process, wherein the oxidative dehydrogenation is carried out with the use of nickel pyrophosphate as a catalyst and helium as an inert diluent. The process described in U.S. Pat. No. 3,935,126 relates to the oxidative dehydrogenation in the presence of an alkaline earth metal/nickel/phosphate-catalyst and nitrogen or helium as an inert diluent. U.S. Pat. No. 3,957,897 describes an analogous reaction, however with the use of an alkaline earth metal pyrophosphate-catalyst and helium as an inert diluent.

Most of the catalysts described heretofore are scarcely suitable for use in the commercial production of styrene as they are required to be used together with an inert diluent, such as helium or nitrogen which in turn has to be circulated, with heavy expenditure of energy, or it is necessary for the inert gases to be subjected to low cooling or scrubbing treatment whereby the recovery of styrene is naturally rendered very difficult. A more serious adverse effect encountered with the catalysts described heretofore, which incidentally should be highly selective, resides in their unsatisfactory productivity of at most 135 g of styrene per 1 of catalyst per hour, determinable by gas-chromatographic analysis in smallest apparatus units only. As appears to result from the data given in British Patent Specification No. 1,148,108, the productivity is even as low as 75 g of styrene per liter of catalyst per hour, in the commercial production of styrene.

It is therefore an object of the present invention to provide a process for making oxidic carrier-supported catalysts which are free from the adverse effects described hereinabove and enable ethylbenzene to be subjected to oxidative dehydrogenation to give styrene under technically and commercially attractive conditions.

The present invention relates more particularly to a carrier-supported catalyst comprising oxides of cobalt and phosphorus and at least one of the oxides of molybdenum and potassium, respectively, in the atomic ratio of $Co_1P_{1-2}Mo_{0-0.05}, K_{0-05}$, the oxides being deposited on a porous carrier material.

Preferred features of the present invention provide:
(a) for the carrier material to have a BET-surface area of 0.1 to 500 m$^2$/g, preferably 2 to 200 m$^2$/g;
(b) for the carrier material to be used in the form of particles with a size of 0.01 to 6 mm, preferably 0.01 to 0.2 mm, for use in a flow bed, or 3 to 6 mm for use in a fixed bed;
(c) for the catalyst to contain 2 to 30 weight % of the oxides of cobalt and phosphorus, molybdenum and/or potassium; and
(d) for the catalyst to contain silicic acid or aluminum oxide as the porous carrier material.

The present invention also relates to a process for making the carrier-supported catalyst which comprises:
(a) saturating a dry porous carrier material with water up to 40 to 80% of its predetermined saturation value;
(b) impregnating the carrier material treated as under (a) either at least once with an aqueous solution of water-soluble compounds of cobalt and phosphorus, molybdenum and/or potassium, or repeatedly and successively, each impregnation being interrupted by an intermediary drying period as specified under (c) below, with an aqueous solution of a water-soluble compound of merely one of the elements aforesaid, the aqueous solution being used in either case in a quantity which is at most necessary for complete saturation;
(c) drying the carrier material after each impregnation over a period of 2 to 20 hours at 350° to 500° K.; and
(d) sintering the carrier material treated as described under (a) through (c) over a period of 0.5 to 4 hours at 550° to 1000° K., preferably 600° to 900° K., in a stream of air.

A preferred feature of the present process provides for the carrier material treated as under (a) above to be impregnated at temperatures of 290° to 375° K.

The invention finally relates to the use of the present carrier-supported catalyst in the production of styrene by subjecting ethylbenzene to an oxidative dehydrogenation reaction with molecular oxygen in gas phase, and to the use of the styrene so made.

The present process permits the reaction just described to be effected at high selectivity and productivity. The terms "conversion rate, yield, selectivity and productivity" as used herein are defined as follows:

$$\text{Conversion rate (\%)} = \frac{\text{mol ethylbenzene used per hour} - \text{mol ethylbenzene recovered per hour from reaction product}}{\text{mol ethylbenzene used per hour}} \cdot 100$$

$$\text{Yield (\%)} = \frac{\text{mol styrene obtained per hour} \cdot 100}{\text{mol ethylbenzene used per hour}}$$

$$\text{Selectivity \%} = \frac{\text{yield}}{\text{conversion rate}} \cdot 100$$

$$\text{Productivity} = \frac{\text{g styrene produced}}{\text{liter catalyst per hour}}$$

In making the catalyst of this invention, it is good practice to use, as the water-soluble compounds, water-soluble metal salts and phosphoric acid. Cobalt and potassium are preferably used in the form of their nitrates, but use can also be made of the corresponding chlorides, carbonates and organic acid salts (formates, acetates, citrates). Molybdenum should preferably be used in the form of ammonium molybdate, especially ammonium heptamolybdate, or together with potassium molybdate, in solution. It is also possible for the phosphorus and potassium to be jointly used in the form of potassium phosphate.

In preparing the present catalyst, the SiO$_2$ or Al$_2$O$_3$-carrier material, which is preferably used in the form of spheroidal particles, is impregnated with water up to 40 to 80% of its absorbing power. This is done to make it possible for the dissolved catalytically active compounds, which are applied to the carrier jointly with, or separately from, one another and gradually, to concentrate substantially in the surface portions of the catalyst carrier.

With the use of the present carrier-supported catalyst, it is possible to effect the oxidative dehydrogenation of ethylbenzene to give styrene as follows:

Ethylbenzene and oxygen are used in a molar ratio of 1:0.1-1 and passed through or over the catalyst in the presence of 1 to 5 mols of steam and 0-4 mols of an inert gas, such as $N_2$ or $CO_2$ per mol of ethylbenzene, at temperatures of 550° to 1000° K. and under pressures of 1 to 5 bars, in a fixed bed, flow bed or fluidized bed.

The process of this invention will now be described with reference to the accompanying exemplary flow scheme.

Ethyl benzene, pure oxygen or air, steam and, if desired, nitrogen or carbon dioxide, are introduced via a conduit (1) and a heat exchanger (2) into a jacketed reactor (3). Inside the heat exchanger (2), the feed mixture is preheated to 440° to 550° K. Placed in the space formed between the wall of the reactor (3) and its jacket is an electrically heatable sand or salt bath with the aid of which the reaction temperature of 550° to 1000° K., preferably 600° to 900° K., is established. The reaction pressure is maintained at 1 to 5, preferably 1 to 3 bars, by means of an automatic control valve (4). The catalyst is contacted with gaseous feed mixture at a spatial velocity of 100 to 3000, preferably 500 to 1500 h$^{-1}$ (spatial velocity = normal liters (S.T.P.) of feed mixture divided by liter of catalyst inside reactor per hour). This gives a 0.1 to 30 second, preferably 0.5 to 6 second, contact time of the feed mixture with the catalyst. The resulting reaction gases are taken from the reactor (3) through a conduit (5) and a condenser (6). In a separator (7), they are separated into liquid condensate and offgas. The condensed reaction products are removed through a conduit (8), weighed and analyzed gas-chromatographically. The off-gas is allowed to escape from the system through a conduit (9). A gas meter (10) is used to determine the quantity of off-gas of which the composition is determined by gas-chromatography.

The following Examples illustrate the invention.

EXAMPLE 1

580 g of spheroidal $SiO_2$ particles (diameter = 5 mm, BET-surface area = 40 m$^2$/g) were placed in a rotary evaporator, impregnated first with 500 g of water up to 71% of the saturation value and then continuously with a solution of 200 g of water, 55.1 g of $Co(NO_3)_2.6H_2O$, 32.86 g of $H_3PO_4$ of 85% strength, and 2.87 g of $KNO_3$ at a temperature of 370 K. Next, the whole was dried for 16 hours at 400° K. and sintered for 1 hour at 823° K. in a stream of air. The resulting catalyst contained 6.2 weight % of catalytically active elements in the form of their oxides of the composition $Co_1P_{1.5}K_{0.15}O_{5.325}$.

EXAMPLE 2

The procedure was as in Example 1. 600 g of spheroidal $SiO_2$ particles (diameter = 5 mm; BET-surface area = 45 m$^2$/g) were impregnated first with 400 g of water, corresponding to 45% of the saturation value, and then with a solution of 490 g of water, 200.9 g of $Co(NO_3)_2.6H_2O$, 119.4 g of $H_3PO_4$ of 85% strength and 1.21 g of $(NH_4)_6Mo_7O_{24}.4H_2O$. Next, the whole was dried (16 h/400° K.) and sintered (1 h/823° K.). The resulting catalyst contained 18 weight % of catalytically active ingredients of the composition $Co_1P_{1.5}Mo_{0.01}O_{5.28}$.

EXAMPLE 3

400 g of SiO particles (diameter = 0.01-0.2 mm; BET-surface area = 180 m$^2$/g) were placed in a bag of plastics material and impregnated therein initially with 200 g of water, corresponding to 50% of the saturation value. Next a solution of 600 g of water, 65.4 g of $Co(NO_3)_2.6H_2O$, 38.8 g of $H_3PO_4$ of 85% strength, 3.42 g of $KNO_3$ and 0.39 g of $(NH_4)_6Mo_7O_{24}.4H_2O$ was applied in three operations at 295° K. and kneaded with the carrier. After each application, the catalyst mass was dried for 2 hours at 400° K. The whole was finally sintered for 1 h at 823° K. in a stream of air. The resulting catalyst contained 10 weight % of catalytically active ingredients of the composition $Co_1P_{1.5}Mo_{0.01}K_{0.15}O_{5.355}$.

EXAMPLE 4

The procedure was as in Example 3. 630 g of $Al_2O_3$-particles (diameter = 0.01 to 0.2 mm; BET-surface area = 20 m$^2$/g) were impregnated initially with 250 g of water, corresponding to 56% of the saturation value and then with a solution of 200 g of water, 164.8 g of $Co(NO_3)_2.6H_2O$, 97.8 g of $H_3PO_4$ of 85% strength and 8.54 g of $KNO_3$. The drying and sintering steps were as in Example 3. The resulting catalyst contained 15.3 weight % of catalytically active ingredients of the composition $Co_1P_{1.5}K_{0.15}O_{5.325}$.

EXAMPLE 5

512 g (1 liter) of the catalyst of Example 1 with the composition $Co_1P_{1.5}K_{0.15}O_{5.325}$ was placed in a fixed bed reactor (capacity = 1.2 liter; filling height = 121 cm) and contacted therein per hour with 1440 normal liters of a mixture of 13 volume % of ethylbenzene, 31 volume % of air and 56 volume % of steam. 37% of the ethylbenzene underwent conversion under a pressure of 2.5 bars inside the reactor, at a reaction temperature of 819° K. and a contact time of 2.1 seconds. Styrene was obtained in a yield of 30.8%. The selectivity was 83.3% and the productivity was 270 g of styrene per liter of catalyst per hour.

EXAMPLE 6

595 g (1 liter) of the catalyst of Example 2 with the composition $Co_1P_{1.5}Mo_{0.01}O_{5.28}$ was placed in a fixed bed reactor and contacted therein per hour with 1004 normal liters of a mixture of 12.6 volume % of ethylbenzene, 31.6 volume % of air and 55.8 volume % of steam. 39.3% of the ethylbenzene underwent conversion under a pressure of 1.1 bars inside the reactor, at a reaction temperature of 784° K. and a contact time of 1.3 seconds. Styrene was obtained in a yield of 33.7%, corresponding to a 85.7% selectivity for styrene. The productivity was 199 g of styrene per liter of catalyst per hour.

EXAMPLE 7

382 g (0.9 liter) of the catalyst of Example 3 with the composition $Co_1P_{1.5}Mo_{0.01}K_{0.15}O_{5.355}$ was placed in a fluidized bed reactor (reaction space = 2 liters; filling height = 50 cm) and contacted therein per hour with 853 normal liters (spatial velocity = 948 h$^{-1}$) of a mixture of 13.2 volume % of ethylbenzene, 31.2 volume % of air and 55.6 volume % of steam. 40.3% of the ethylbenzene underwent conversion under a pressure of 1.1 bars inside the reactor at a reaction temperature of 848° K. and a contact time of 1.3 seconds. Styrene was obtained in a yield of 35.5%, corresponding to a 88.2% selectivity for styrene. The productivity was 205 g of styrene per liter of catalyst per hour.

EXAMPLE 8

640 g (0.8 liter) of the catalyst of Example 4 with the composition $Co_1P_{1.5}K_{0.15}O_{5.325}$ was placed in a fluidized bed reactor and contacted therein per hour with 1040 normal liters (spatial velocity = 1300 $h^{-1}$) of a mixture of 12.6 volume % of ethylbenzene, 30 volume % of air and 57.4 volume % of steam. 32.4% of the ethylbenzene underwent conversion under a pressure of 1.1 bars inside the reactor, at a reaction temperature of 764° K. and a contact time of 1.2 seconds. Styrene was obtained in a yield of 28%. The selectivity was 86.3% and the productivity 213 g of styrene per liter of catalyst per hour.

We claim:

1. A carrier-supported catalyst comprising oxides of cobalt and phosphorus and at least one of the oxides of molybdenum and potassium in the atomic ratio of $Co_1P_{1-2}Mo_{0-0.05}K_{0-05}$ on a porous carrier material.

2. A carrier-supported catalyst as claimed in claim 1, wherein the carrier material has a BET-surface area of 0.1 to 500 m²/g.

3. A carrier-supported catalyst as claimed in claim 1, wherein the carrier material consists of particles with a size of 0.01 to 6 mm.

4. A carrier-supported catalyst as claimed in claim 1, wherein the carrier material consists of particles with a size of 0.01 to 0.2 mm for use in flow bed.

5. A carrier-supported catalyst as claimed in claim 1, wherein the carrier material consists of particles with a size of 3 to 6 mm for use in a fixed bed.

6. A carrier-supported catalyst as claimed in claim 1, containing 2 to 30 weight % of the oxides of cobalt and phosphorus and at least one of the elements selected from molybdenum and potassium.

7. A carrier-supported catalyst as claimed in claim 1, containing silicic acid or aluminum oxide as the porous carrier material.

8. A process for making a carrier-supported catalyst as claimed in claim 1, which comprises:
   (a) saturating a dry porous carrier material with water up to 40 to 80% of its predetermined saturation value;
   (b) impregnating the carrier material treated as under (a) either at least once with an aqueous solution of water-soluble compounds of cobalt and phosphorus, and at least one of the elements selected from molybdenum and potassium, or repeatedly and successively, each impregnation being interrupted by an intermediary drying period as specified under (c), with an aqueous solution of a water-soluble compound of merely one of the elements aforesaid, the aqueous solution being used in either case in a quantity which is at most necessary for complete saturation.
   (c) drying the carrier material after each impregnation over a period of 2 to 20 hours at 350° to 500° K.; and
   (d) sintering the carrier material treated as described under (a) through (c) over a period of 0.5 to 4 hours at 550° to 1000° K., in a stream of air.

9. A process as claimed in claim 8, wherein the carrier material treated as described under (a) is impregnated as described under (b) at temperatures of 290° to 375° K.

* * * * *